United States Patent
Filatov et al.

(10) Patent No.: US 12,073,407 B1
(45) Date of Patent: Aug. 27, 2024

(54) ENHANCED DATA SECURITY AND PRESENTATION SYSTEM AND METHOD

(71) Applicant: VISA INTERNATIONAL SERVICE ASSOCIATION, San Francisco, CA (US)

(72) Inventors: Alexander Filatov, Moscow (RU); Elena Valetova, Moscow (RU); Fazluddin Iqbal Dawood, Dubai (AE); Charles Campbell, Dubai (AE); Ghanashyama Mahanty, Dubai (AE); Anthony Dell, Dubai (AE); Ilya Zabegaev, Moscow (RU)

(73) Assignee: Visa International Service Association, San Francisco, CA (US)

( * ) Notice: Subject to any disclaimer, the term of this patent is extended or adjusted under 35 U.S.C. 154(b) by 0 days.

(21) Appl. No.: 17/954,848

(22) Filed: Sep. 28, 2022

Related U.S. Application Data

(63) Continuation of application No. 17/266,031, filed as application No. PCT/US2018/046777 on Aug. 14, 2018, now Pat. No. 11,494,778.

(51) Int. Cl.
  *G06Q 20/40* (2012.01)
  *G06Q 40/03* (2023.01)
  *G16H 10/65* (2018.01)

(52) U.S. Cl.
  CPC ......... *G06Q 20/4016* (2013.01); *G06Q 40/03* (2023.01); *G16H 10/65* (2018.01)

(58) Field of Classification Search
  CPC .................................................. G06Q 40/03
  See application file for complete search history.

(56) References Cited

U.S. PATENT DOCUMENTS

| | | | |
|---|---|---|---|
| 7,464,859 B1 | 12/2008 | Hawkins | |
| 7,873,566 B1 * | 1/2011 | Templeton | G06Q 40/03 |
| | | | 705/45 |
| 7,925,576 B2 * | 4/2011 | Swift | G06Q 20/02 |
| | | | 705/45 |
| 9,916,578 B2 | 3/2018 | Dominguez | |

(Continued)

FOREIGN PATENT DOCUMENTS

| | | |
|---|---|---|
| RU | 2181216 C1 | 4/2002 |
| RU | 2509362 C2 | 3/2014 |

OTHER PUBLICATIONS

Application No. SG11202101350S , Written Opinion, Mailed On Nov. 7, 2022, 6 pages.

(Continued)

*Primary Examiner* — Bennett M Sigmond
*Assistant Examiner* — Marla Hudson
(74) *Attorney, Agent, or Firm* — Kilpatrick Townsend & Stockton LLP

(57) ABSTRACT

Disclosed are systems, methods, apparatuses, and computer readable media for quickly and efficiently providing individual-level scores that are serve as more-accurate predictions of a target event. These predictions are made using a model that factors specific variables based on transaction attributes gathered from transaction data for the individual, which may be exclusive to certain entities. These individual-level scores can be updated and periodically uploaded to an entity (e.g., a reporting agency) that can utilize existing infrastructure to quickly provide these scores to any requesters.

20 Claims, 10 Drawing Sheets

(56) References Cited

U.S. PATENT DOCUMENTS

| | | | |
|---|---|---|---|
| 11,379,913 B1* | 7/2022 | Perelli-Minetti | G06Q 40/125 |
| 2003/0236728 A1 | 12/2003 | Sunderji et al. | |
| 2005/0125351 A1 | 6/2005 | Tidwell et al. | |
| 2006/0229974 A1* | 10/2006 | Keithley | G06Q 40/03 |
| | | | 705/38 |
| 2007/0138257 A1* | 6/2007 | Dragt | G06Q 20/102 |
| | | | 235/379 |
| 2010/0125547 A1 | 5/2010 | Barrett et al. | |

OTHER PUBLICATIONS

Application No. PCT/US2018/046777, International Preliminary Report on Patentability, Mailed On Feb. 9, 2021, 9 pages.
Application No. PCT/US2018/046777, International Search Report and Written Opinion, Mailed On May 14, 2019, 14 pages.
Application No. RU2021106378, Office Action, Mailed On Feb. 17, 2022, 24 pages.

\* cited by examiner

| Feature Type | | Feature | Variable Type |
|---|---|---|---|
| Card | 302 | Number of months since first transaction; if >12 then '12' | Single Variable |
| | 304 | Bank Relations; if appl. Issuer is main in terms of tx count over last 12 months then '1', else '0' | Single Variable |
| Transactions | 306 | Activation in top risk MCCs; at least 1 tx at pawn shops, betting, security brokers over last 12 months then '1', else '0' | Cross Variable — 320 |
| | 308 | Average ticket size in POS tx for last 12 months | |
| | 310 | Share of medical (specific MCCs) volume out of all POS tx during last 12 months | Cross Variable — 322 |
| | 312 | Share of construction (specific MCCs) volume out of all POS tx during last 12 months | |
| | 314 | Upscale consistency; number of months with at least one tx in upscale (specific MCCs) | Cross Variable — 324 |
| Authorizations | 316 | Insufficient funds decline rate; average number of insufficient funds declines per active month | |

FIG. 3

SIGMA (
Intercept +
(ATS>0) × beta_1 +
(ATS>300) × beta_2 +
(ATS>400) × beta_3 +
(ATS>600) × beta_4 +
(months_with_Visa>0) × gamma_1 +
(months_with_Visa>6) × gamma_2 +
(upscale>0) × delta_1 +
(upscale>1) × delta_2 +
(upscale>2) × delta_3 +
(upscale>3) × delta_4 +
(upscale>4) × delta_5 +
(upscale>5) × delta_6 +
relationship × epsilon +
(share>0) × zeta_1 + (share>1) × zeta_2 )
= PROBABILITY_OF_DEFAULT

FIG. 4

| Feature Type | | Feature | Ex. #1 | Ex. #2 |
|---|---|---|---|---|
| Card | 302 | Number of months since first transaction; if >12 then '12' | 13 months | 3 months |
| | 304 | Bank Relations; if appl. Issuer is main in terms of tx count over last 12 months then '1', else '0' | Main | Not Main |
| Transactions | 306 | Activation in top risk MCCs; at least 1 tx at pawn shops, betting, security brokers over last 12 months then '1', else '0' | Not Active | Active |
| | 308 | Average ticket size in POS tx for last 12 months | 700P | 332P |
| | 310 | Share of medical (specific MCCs) volume out of all POS tx during last 12 months | 0.1 | 0.18 |
| | 312 | Share of construction (specific MCCs) volume out of all POS tx during last 12 months | 0.02 | 0.01 |
| | 314 | Upscale consistency; number of months with at least one tx in upscale (specific MCCs) | 9 | 1 |
| Authorizations | 316 | Insufficient funds decline rate; average number of insufficient funds declines per active month | 0 | 1.5 |

FIG. 5

| Feature Type | | Feature | Ex. #1 | Ex. #2 |
|---|---|---|---|---|
| Card | 302 | Number of months since first transaction; if >12 then '12' | >6 | >0 |
| | 304 | Bank Relations; if appl. Issuer is main in terms of tx count over last 12 months then '1', else '0' | 1 | 0 |
| Transactions | 306 | Activation in top risk MCCs; at least 1 tx at pawn shops, betting, security brokers over last 12 months then '1', else '0' | | |
| | 308 | Average ticket size in POS tx for last 12 months | GR = 600 | GR = 300 |
| | 310 | Share of medical (specific MCCs) volume out of all POS tx during last 12 months | GR = 100 | GR = 100 |
| | 312 | Share of construction (specific MCCs) volume out of all POS tx during last 12 months | | |
| | 314 | Upscale consistency; number of months with at least one tx in upscale (specific MCCs) | GR = 6 | GR = 1 |
| Authorizations | 316 | Insufficient funds decline rate; average number of insufficient funds declines per active month | | |

FIG. 6

| Parameter | Value | Coefficient | E.g. #1 | E.g. #2 |
|---|---|---|---|---|
| Intercept | 0 | -5.00 | 1 | 1 |
| ATS | 300 | 0.91 | | 1 |
| | 400 | 0.66 | 1 | |
| | 600 | 0.23 | | |
| month_with_Visa | 0 | 0.48 | 1 | 1 |
| | 6 | 0.18 | | |
| upscale | 0 | 1.23 | | |
| | 1 | 0.98 | | 1 |
| | 2 | 0.87 | | |
| | 3 | 0.76 | | |
| | 4 | 0.65 | | |
| | 5 | 0.43 | 1 | |
| relationship | 0 | 0.21 | | |
| share | 0 | 0.55 | 1 | 1 |
| | 1 | 0.33 | | |
| | | Linear Score | -3.83 | -2.34 |
| | | Probability | 0.02 | 0.09 |
| | | Default Score | 776 | 668 |

FIG. 7

ENHANCED DATA SECURITY AND PRESENTATION SYSTEM AND METHOD

CROSS REFERENCE TO RELATED APPLICATIONS

This application is a continuation application of U.S. patent application Ser. No. 17/266,031, filed Feb. 4, 2021, which is a National Stage of International Application No. PCT/US2018/046777 filed Aug. 14, 2018, of which are herein incorporated by in its entirety.

BACKGROUND

Many business entities may desire certain information about their customers before deciding to enter into transactions with them. For instance, it may be desirable to perform a credit check for a customer before performing a transaction by inquiring a credit reporting agency for information about the customer (e.g., a credit score, the likelihood the customer will default, and so forth).

In return, the credit reporting agency may provide that information, which is often based on their own proprietary models. This turnaround time can be very quick (e.g., seconds). However, these credit reporting agencies do not have access to all available pertinent information. For instance, they would not have access to data associated with individual transactions previously made by the customer with a payment account. Some of that data can be very pertinent and, when factored in, can greatly improve the accuracy of the information (e.g., a better predicted likelihood the customer will default) that is requested by the business entity.

At the same time, for security and privacy purposes, it would be undesirable to grant the credit reporting agency free access to such personal data. Thus, a problem exists for how to enable the transaction data associated with a customer to be factored into the models of the credit reporting agency without granting the credit reporting agency access to that data, without compromising the quick turnaround time expected by the business entities.

Embodiments of the present invention are directed to methods and systems of data communication between mobile devices and access devices. Embodiments of the invention address these and other problems, individually and collectively.

BRIEF SUMMARY

Embodiments of the present invention are directed to systems, methods, apparatuses, and computer readable media for quickly and efficiently providing individual-level scores that are serve as more-accurate predictions of a target event. These predictions are made using a model that factors specific variables based on transaction attributes gathered from transaction data that may be exclusive to certain entities. In some embodiments, these transaction attributes are associated with transactions made using a payment account (e.g., an credit card account) with a particular entity. The individual-level scores can be calculated by that entity, but uploaded elsewhere (e.g., to a database associated with a credit reporting agency) in order to leverage existing infrastructure for the quick return of individual-level scores upon request.

In some embodiments, a method is disclosed that includes receiving from a plurality of issuers, at a first data processing system, data associated with a first set of individuals. The data may include one or more hashed account identifiers for each individual in the first set of individuals. The method may further include assigning, by the first data processing system, a unique user identifier (UUID) to each individual in the first set of individuals. The method may further include storing, by the first data processing system, the data for each individual in the first set of individuals based on the UUID for the respective individual. The method may further include transmitting, by the first data processing system to a second data processing system, for each individual in the first set of individuals: the one or more hashed account identifiers for the respective individual, the UUID for the respective individual, and target event data. The second data processing system may collect transaction data associated with each individual in the first set of individuals and apply a predictive model to the transaction data associated with each individual in the first set of individuals in order to calculate an individual-level score associated with the respective individual.

In various embodiments, the predictive model may be configured to determine a predicted default rate for an individual based on a set of transactional attributes in the transaction data associated with the respective individual. The set of transactional attributes may include two or more of: a number of months since a first transaction performed by the respective individual; a bank relation associated with the respective individual; a top risk activation indication associated with the respective individual, wherein the top risk activation indication is based on any transactions with high-risk merchants performed over the last twelve months by the respective individual; an average ticket size for all transactions performed over the last twelve months by the respective individual; a share of medical-related transactions out of all transactions performed over the last twelve months by the respective individual; a share of construction-related transactions out of all transactions performed over the last twelve months by the respective individual; a number of months with at least one upscale transaction performed by the respective individual; and an average number of insufficient funds declines per active month experienced by the respective individual.

In various embodiments, the method may further include receiving from a plurality of issuers, at the first data processing system, updated data associated with the first set of individuals. In various embodiments, the method may further include storing, by the first data processing system, the updated data for each individual in the first set of individuals based on the UUID for the respective individual. In various embodiments, the method may further include transmitting, by the first data processing system to the second data processing system, the updated data for each individual in the first set of individuals. In various embodiments, the target event data includes any past default events associated with the respective individual.

In some embodiments, a computer system is disclosed that includes a processor and a computer-readable memory containing program instructions that, when executed by the processor, cause the processor to: receive from a plurality of issuers, at a first data processing system, data associated with a first set of individuals. The data may include one or more hashed account identifiers for each individual in the first set of individuals. The program instructions when executed by the processor, may further cause the processor to assign, by the first data processing system, a unique user identifier (UUID) to each individual in the first set of individuals. The program instructions when executed by the processor, may further cause the processor to store, by the first data processing system, the data for each individual in the first set of individuals based on the UUID for the respective individual. The program instructions when executed by the processor, may further cause the processor to transmit, by the first data processing system to a second data processing system, for each individual in the first set of individuals: the one or more hashed account identifiers for the respective individual; the UUID for the respective individual; and target event data. In some embodiments, the second data processing system collects transaction data associated with each individual in the first set of individuals and applies a predictive model to the transaction data associated with each individual in the first set of individuals in order to calculate an individual-level score associated with the respective individual.

In various embodiments, the predictive model is configured to determine a predicted default rate for an individual based on a set of transactional attributes in the transaction data associated with the respective individual. The set of transactional attributes may include two or more of: a number of months since a first transaction performed by the respective individual; a bank relation associated with the respective individual; a top risk activation indication associated with the respective individual, wherein the top risk activation indication is based on any transactions with high-risk merchants performed over the last twelve months by the respective individual; an average ticket size for all transactions performed over the last twelve months by the respective individual; a share of medical-related transactions out of all transactions performed over the last twelve months by the respective individual; a share of construction-related transactions out of all transactions performed over the last twelve months by the respective individual; a number of months with at least one upscale transaction performed by the respective individual; and an average number of insufficient funds declines per active month experienced by the respective individual.

In various embodiments, the program instructions when executed by the processor, may further cause the processor to receive from a plurality of issuers, at the first data processing system, updated data associated with the first set of individuals; and store, by the first data processing system, the updated data for each individual in the first set of individuals based on the UUID for the respective individual. In various embodiments, the target event data includes any past default events associated with the respective individual.

In some embodiments, a method is disclosed that includes receiving a plurality of scores corresponding one-to-one with a plurality of individuals, wherein each score of the plurality of scores is determined by applying a predictive model configured to determine a predicted default rate associated with the individual. The predictive model may be further configured to utilize data associated with the respective individual including values of a first set of transactional attributes, the first set of transactional attributes including two or more of: a number of months since a first transaction performed by the respective individual; a bank relation associated with the respective individual; a top risk activation indication associated with the respective individual, wherein the top risk activation indication is based on any transactions with high-risk merchants performed over the last twelve months by the respective individual; an average ticket size for all transactions performed over the last twelve months by the respective individual; a share of medical-related transactions out of all transactions performed over the last twelve months by the respective individual; a share of construction-related transactions out of all transactions performed over the last twelve months by the respective individual; a number of months with at least one upscale transaction performed by the respective individual; and an average number of insufficient funds declines per active month experienced by the respective individual. The method may further include storing the plurality of scores in a database. The method may further include receiving, from an issuer, a request for a score for an individual. The method may further include locating the score for the individual among the plurality of scores in the database. The method may further include sending, to the issuer, the requested score for the individual.

In various embodiments, the method may further include receiving an updated plurality of scores corresponding one-to-one with the plurality of individuals; and updating the plurality of scores in the database based on the updated plurality of scores. In various embodiments, the request for the score for the individual includes a unique user identifier (UUID) associated with the individual, and the score for the individual is stored in the database based on the UUID associated with the individual. In various embodiments, the receiving, locating, and sending steps of the method are performed within a total of three seconds. In various embodiments, the plurality of scores are factored into a combined scoring model to obtain a plurality of combined scores corresponding one-to-one with the plurality of individuals.

In some embodiments, a computer system is disclosed that includes a processor and a computer-readable memory containing program instructions that, when executed by the processor, cause the processor to: receive a plurality of scores corresponding one-to-one with a plurality of individuals. Each score of the plurality of scores may be determined by applying a predictive model configured to determine a predicted default rate associated with the individual, and the predictive model may be further configured to utilize data associated with the respective individual including values of a first set of transactional attributes. The first set of transactional attributes may include two or more of: a number of months since a first transaction performed by the respective individual; a bank relation associated with the respective individual; a top risk activation indication associated with the respective individual, wherein the top risk activation indication is based on any transactions with high-risk merchants performed over the last twelve months by the respective individual; an average ticket size for all transactions performed over the last twelve months by the respective individual; a share of medical-related transactions out of all transactions performed over the last twelve months by the respective individual; a share of construction-related transactions out of all transactions performed over the last twelve months by the respective individual; a number of months with at least one upscale transaction performed by the respective individual; and an average number of insufficient funds declines per active month experienced by the respective individual. In some embodiments, the program instructions, when executed by the processor, may further cause the processor to store the plurality of scores in a database. In some embodiments, the program instructions, when executed by the processor, may further cause the processor to receive, from an issuer, a request for a score for an individual. In some embodiments, the program instructions, when executed by the processor, may further cause the processor to locate the score for the individual among the plurality of scores in the database. In some embodiments, the program instructions, when executed by the processor, may further cause the processor to send, to the issuer, the requested score for the individual.

In various embodiments, a computer system is disclosed that includes a processor and a computer-readable memory containing program instructions that, when executed by the processor, further cause the processor to: receive an updated plurality of scores corresponding one-to-one with the plurality of individuals and update the plurality of scores in the database based on the updated plurality of scores. In some embodiments, the request for the score for the individual includes a unique user identifier (UUID) associated with the individual, and the score for the individual is stored in the database based on the UUID associated with the individual. In various embodiments, the receiving, locating, and sending steps are performed within a total of three seconds. In various embodiments, the plurality of scores are factored into a combined scoring model to obtain a plurality of combined scores corresponding one-to-one with the plurality of individuals. In various embodiments, the requested score for the individual is the combined score associated with the individual.

These and other embodiments of the invention are described in further detail below.

BRIEF DESCRIPTION OF THE DRAWINGS

FIG. 3 is a chart of certain transaction attributes used in calculating individual-level scores, in accordance with certain embodiments.

FIG. 4 illustrates an example formula for calculating individual-level scores, in accordance with certain embodiments.

FIG. 5 illustrates example transaction attribute values for individuals that are used in the individual-level score calculation, in accordance with certain embodiments.

FIG. 6 illustrates the corresponding single variable and cross-variable bins and values used in the individual-level score calculation for the transactional values shown in FIG. 5, in accordance with certain embodiments.

FIG. 7 illustrates example individual-level calculations based on the corresponding single variable and cross-variable bins shown in FIG. 6, in accordance with certain embodiments.

DETAILED DESCRIPTION

Figure 1:
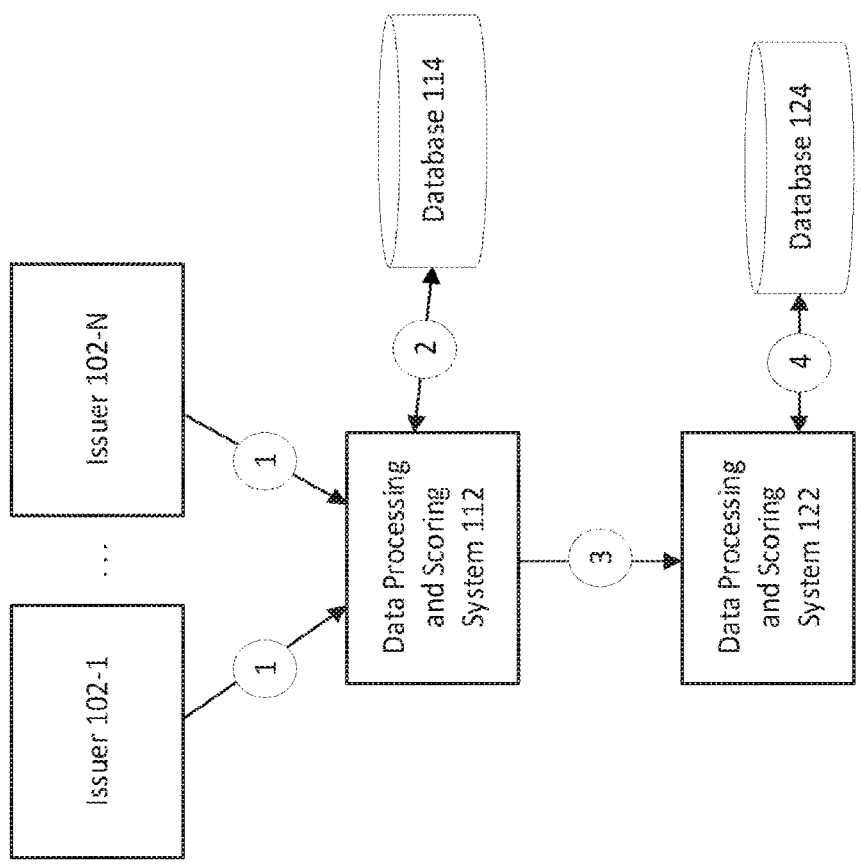
FIG. 1 is a system diagram that shows a process flow for data collection, in accordance with certain embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Embodiments of the present invention are directed to systems, methods, apparatuses, and computer readable media for quickly and efficiently providing individual-level scores that are serve as more-accurate predictions of a target event. These predictions are made using a model that factors specific variables based on transaction attributes gathered from transaction data that may be exclusive to certain entities. In some embodiments, these transaction attributes are associated with transactions made using a payment account (e.g., an credit card account) with a particular entity. The individual-level scores can be calculated by that entity, but uploaded elsewhere (e.g., to a database associated with a credit reporting agency) in order to leverage existing infrastructure for the quick return of individual-level scores upon request.

Prior to discussing embodiments of the invention, description of some terms may be helpful in understanding embodiments of the invention.

An "Account identifier" or "Primary account number (PAN)" may include a reference number to an account (e.g. a payment account and/or payment device associated with the account).

The term "computer" as used herein refers to a system comprising a processor and a computer readable medium, such as computer memory or other data storage device, coupled to the processor. The computer readable medium stores code executable by the processor.

The term "server computer" may include a powerful computer or cluster of computers. For example, the server computer can be a large mainframe, a minicomputer cluster, or a group of servers functioning as a unit. In one example, the server computer may be a database server coupled to a Web server. The server computer may be coupled to a database and may include any hardware, software, other logic, or combination of the preceding for servicing the requests from one or more client computers. The server computer may comprise one or more computational apparatuses and may use any of a variety of computing structures, arrangements, and compilations for servicing the requests from one or more client computers.

"Processing logic" may refer to any suitable data computation device or devices such as a processor, field-programmable gate array, or otherwise. A processor may comprise one or more microprocessors working together to accomplish a desired function. The processor may include a CPU comprising at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

A "memory" may be any suitable device or devices that can store electronic data. A suitable memory may comprise a non-transitory computer readable medium that stores instructions that can be executed by a processor to implement a desired method. Examples of memories may comprise one or more memory chips, disk drives, etc. Such memories may operate using any suitable electrical, optical, and/or magnetic mode of operation.

An "issuer" is typically a business entity (e.g., a bank or credit union) which issues a payment device (such as a credit card, debit card, smart card, prepaid device or contactless device) to an account owner (e.g., customer) and which provides administrative and management functions for the payment account. A payment account may be any account usable in a transaction, such as a credit, debit or prepaid account.

FIG. 1 is a system diagram that shows a process flow for data collection. In some embodiments, there may be one or more Issuers 102-1 to 102-N.

In some embodiments, the Data Processing and Scoring System 112 may be configured to perform communications with the one or more Issuers 102-1 to 102-N. In some embodiments, Data Processing and Scoring System 112 may be associated with an entity, such as a credit reporting agency, and the issuers may request credit checks from the credit reporting agency pertaining to customers of the issuers. There may be a Database 114 associated with the Data Processing and Scoring System 112. The Data Processing and Scoring System 112 may be an example of a first data processing system.

In some embodiments, the Data Processing and Scoring System 122 may be configured to perform communications with the one or more Issuers 102-1 to 102-N. In some embodiments, Data Processing and Scoring System 122 may be associated with an entity, such as a transaction processor (e.g., a processor of Credit Card transactions), that would have access to transaction data for the various individuals that it processes transactions for. There may be a Database 124 associated with the Data Processing and Scoring System 122. The Data Processing and Scoring System 122 may be an example of a second data processing system.

During the data collection process, at step 1, the Data Processing and Scoring System 112 may request customer data from the one or more Issuers 102-1 to 102-N. For each issuer, this data may include information associated with that issuer's customers, such as customer identities, account identifiers or personal account numbers (PANs), and card expiration dates associated with those customers. In some embodiments, a customer's identity may include national passport data. In some embodiments, a customer's PAN may be received in hashed form (e.g., a hashed account identifier) and may include PANs associated with credit card and/or debit cards of the customer. In some embodiments, the PANs may be hashed using HMAC-SHA256. In some embodiments, the client passport data and card expiration dates may also be received in hashed form, such as using a hash algorithm such as HMAC/or/SHA256. Sending the actual (e.g., unhashed) values of each customer's data (e.g., their passport data, PANs, and card expiration dates) is not necessarily needed because this data is primarily used for matching purposes, such as to aggregate all the data for a specific, unique individual who may be a customer of many of the Issuers 102-1 to 102-N. Hashed values are sufficient for this purpose and can provide additional security. This is described in additional detail below.

At step 2, the Data Processing and Scoring System 112 may take the received data and create a unique identity for each unique individual, such that data collected from different sources for a single individual can be aggregated and stored within the Database 114. Since an individual may be a customer of more than one issuer, some of the data received from different issuers may pertain to a single individual. For instance, there may be an individual (e.g., "John Smith") who is a customer of both Issuer 102-1 and Issuer 102-N. The Data Processing and Scoring System 112 may receive data from Issuer 102-1 that contains information associated with "John Smith" and also data from Issuer 102-N that contains information associated with "John Smith". All of this data should be stored in a way that associates the data with the same individual. However, storing the data based on individual name may be insufficient; there may be many individuals named "John Smith". In order to identify data pertaining to a unique individual, the Data Processing and Scoring System 112 may match the hashed client passport data received from the different issuers. In some embodiments, the Data Processing and Scoring System 112 may create a Unique User Identity (UUID) for each unique individual and associate all the data received for that particular individual with their UUID.

For instance, both Issuer 102-1 and Issuer 102-N may each have data that is associated with hashed passport data with a value of "mdfj107k". Thus, all of this data would be associated with a single unique individual. That individual would be assigned a UUID and the data from both Issuer 102-1 and Issuer 102-N (e.g., all of the hashed PANs) would be stored under that UUID. In some embodiments, the Data Processing and Scoring System 112 may link all data for an individual, including the hashed PANs associated with that individual. Other data for the individual may include hashes of personal data for the individual, such as hashes of real passport data, name of the individual, contact data for the individual, and so forth. In some embodiments, the Data Processing and Scoring System 112 may also collect, aggregate, and store historical data for target events (described below) associated with each individual under their corresponding UUID. The Data Processing and Scoring System 112 may store all of this information in the associated Database 114. It is important to note that the Data Processing and Scoring System 112 and the Database 114 do not contain actual PANs—only the hashed PANs.

At step 3, the Data Processing and Scoring System 112 may feed data in the associated Database 114 to the Data Processing and Scoring System 122. This data will contain information about the various individuals, including each individual's UUID, their respective hashed PANs, but not any personal data associated with the individuals (e.g., actual or hashed values associated with real passport data, names, contact information). In some embodiments, the PANs may be hashed using HMAC-SHA256. Sending the actual or hashed values of personal data (e.g., passport data, names, contact information) is not necessarily needed because the hashed PANs can be used for matching purposes against hashed PANs known by the Data Processing and Scoring System 122 (e.g., to aggregate all the transaction data associated with PANs for specific, unique individual who may be a customer of many of the Issuers 102-1 to 102-N).

In some embodiments, the Data Processing and Scoring System 112 may also provide country-level, statistically-valid samples of target events associated with various individuals (e.g., based on UUID). In some embodiments, the target events may include early payment default, delinquency >90 days at 12 MOB, and so forth. These target events may already be known to the Data Processing and Scoring System 112 (e.g., such as if Data Processing and Scoring System 112 is associated with a credit reporting agency). Since this information represents known, historical outcomes, it is relevant to the Data Processing and Scoring System 122 for building the predictive model (e.g., as training data in a supervised machine learning model) used to determine the likelihood for a future target event associated with a given individual. Thus, for a given individual, the Data Processing and Scoring System 112 would be sending that individual's UUID, that individual's hashed PANs, and historical data for any target events associated with that individual (if those target events exist for the individual).

For instance, assume that, in the United States, there is a global list of unique individuals whose data is maintained by the Data Processing and Scoring System 112. To simplify further, consider that a subset of these individuals may include individual A (with UUID of "1234"), individual B (with UUID of "1235"), and individual C (with UUID of "1236"). There may be historical target event data associated with these individuals, such as defaults. For example, individual A and individual B may have defaulted at some time in the past, while individual C has never defaulted. All of this information can be sent to the Data Processing and Scoring System 122, which may have access to transaction data associated with individuals A, B, and C (including their historical transaction data leading up to the default events). The Data Processing and Scoring System 122 may be tasked with generating a predictive model for determining the likelihood of default based on the transaction data for an individual. This involves determining the factors (e.g., "transactional attributes" or transaction patterns from the transaction data) that are predictors of default and how each those factors impact the occurrence of default. In more concrete terms, this would involve determining various factors (e.g., "transactional attributes") in the historical transaction data for individuals A and B (who are known to have defaulted in the past) leading up to their default events that are not present for individual C (who did not default), and then determining the individual impact of each of those factors. Some of the transactional attributes may correspond to a single variable in the model, while other transactional attributes may be combined into cross-variables in the model. The model can then be verified by applying it to transaction data for a test sample of individuals not used to generate the model for whom the target events are known (e.g., applying it to individual D that is known to have defaulted in the past) to see if the model accurately predicts the target event based on the transaction data (e.g., the model ends up accurately predicting that individual D is highly likely to default based on the transaction patterns that existed leading up to the actual default event). Examples of model generation may include various regressions, such as piecewise linear regression, through which the individual impact (e.g., coefficients) for the different variables (obtained based on the transactional attributes determined from the transaction data) that are predictive of likelihood of the target event occurring (e.g., default) can be determined.

At step 4, the Data Processing and Scoring System 122 may aggregate transaction data for each individual at the UUID level. For instance, the Data Processing and Scoring System 122 may be associated with a transaction processor and have access to transaction data associated with various PANs. This information can be contained in one or more internal databases (e.g., including Database 124 or an entirely separate database). A particular individual associated with a UUID may be associated with numerous PANs (e.g., if the individual has numerous accounts) and each PAN may be associated with its own transaction data (e.g., based on transactions made using the account corresponding to that PAN). In order to aggregate all the transaction data for an individual at the UUID level, all of the hashed PANs for that individual that were received from the Data Processing and Scoring System 112 can be matched against hashes of the PANs in the one or more internal databases. For any hashed PANs that match, the transaction data associated with that PAN can be collected. Thus, all the available transaction data associated with PANs for a particular individual can be collected and aggregated. In some embodiments, the Data Processing and Scoring System 122 can generate the predictive model at this step if the available data is sufficient (e.g., the target events and transaction data are known for individuals in the entire country), while in other embodiments, the predictive model may have been generated well in advance. In either case, with the predictive model established, the Data Processing and Scoring System 122 can calculate individual-level scores based on applying the predictive model to the transaction data for a particular individual. In some embodiments, the Data Processing and Scoring System 122 may store the calculated individual-level scores in Database 124 (along with other data for the individual, such as the individual's hashed PANs, transaction data, or target events) based on the individual's UUID.

In some embodiments, the data collection process illustrated in FIG. 1 may initially be performed to initialize the various databases (e.g., Database 114 and Database 124), and also periodically for any data updates in order to capture changes in the data. These changes may include changes in passport data, new card issue, replacement of compromised/stolen cards, and so forth. For instance, every five days, the Data Processing and Scoring System 112 may request any new customer data (e.g., established in the last five days) from the one or more Issuers 102-1 to 102-N. The Data Processing and Scoring System 112 may add the updated data to Database 114 and then push any relevant updated data (e.g., excluding any changes to personal data) to the Data Processing and Scoring System 122, which may use the updated data to obtain any missing transaction data and re-calculate individual-level scores. For instance, individual A may have opened a new account with an issuer and have a new PAN. The new hashed PAN can be sent to the Data Processing and Scoring System 122, where it can be used to collect transaction data associated with that PAN. That transaction data can be added to, and aggregated with, the existing transaction data for the individual and used to calculate a new individual-level score for the individual. At no point in either the initial data collection process or updated data collection process would the Data Processing and Scoring System 122 have access to personal data (e.g., real passport data, names, contact information), or either of the Data Processing and Scoring Systems 112 and 122 have access to actual PANs.

Figure 2:
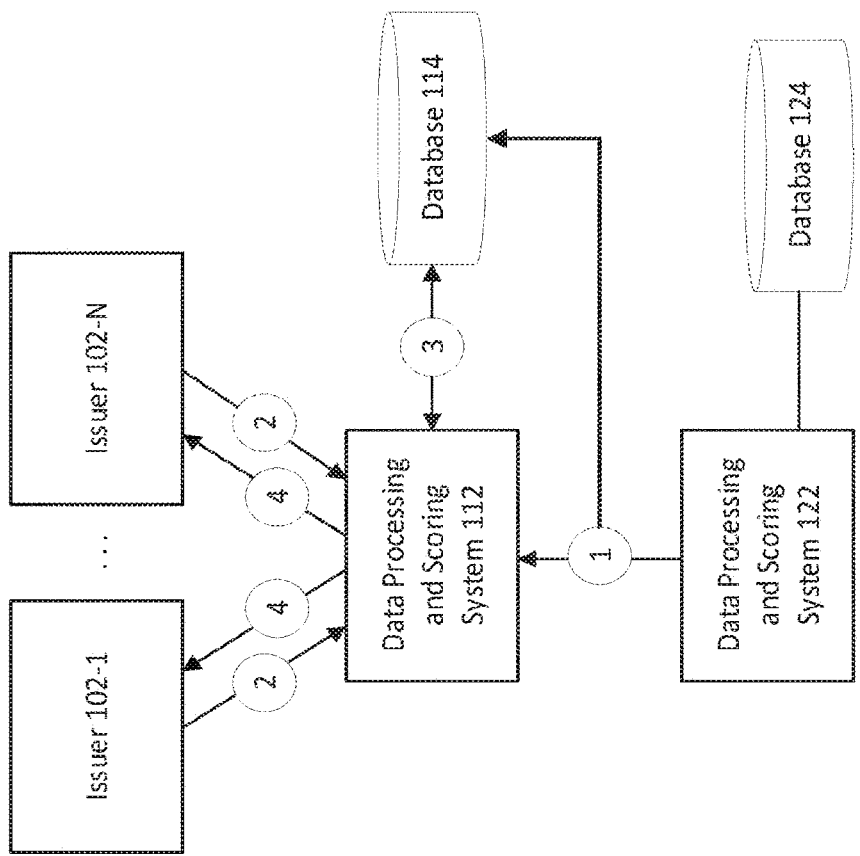
FIG. 2 is a system diagram that shows a process flow for score distribution, in accordance with certain embodiments.

FIG. 2 is a system diagram that shows a process flow for score distribution. As in FIG. 1, there may be one or more Issuers 102-1 to 102-N, a Data Processing and Scoring System 112 associated with a Database 114, and a Data Processing and Scoring System 122 associated with a Database 124.

At step 1, the Data Processing and Scoring System 122 may perform a batch upload of the calculated individual-level scores (which may be stored in Database 124) to the Data Processing and Scoring System 112 for storage in the Database 114. In some embodiments, for each individual, only the UUID and corresponding individual-level scores are shared. No transactional or personally-identifying information is shared. Thus, the Data Processing and Scoring System 112 will have access to the individual-level scores without having to further retrieve them from the Data Processing and Scoring System 122 at a later time. For a particular individual, the Data Processing and Scoring System 112 may use the UUID corresponding to the individual-level score in order to associate and store the individual-level score with other data for that individual that was stored based on UUID (e.g., the hashed passport data).

At step 2, any of the Issuers 102-1 to 102-N may request individual-level scores from the Data Processing and Scoring System 112 using existing integrated channels. In some embodiments, these requests may identify specific individuals associated with the request based on passport data or hashed passport data for the individual(s), as opposed to the UUID (which the issuers may not know, since that is assigned by the Data Processing and Scoring System 112).

At step 3, the Data Processing and Scoring System 112 may match hashed passport data (first hashing the passport data, if it was received unhashed) from the request against the hashed passport data stored in the Database 114, in order to determine the individual(s) being identified with the request. When a match is found, the UUID attached to the matching hashed passport data in Database 114 can then be used to locate all of the other data associated with that UUID and corresponding to that particular individual. Thus, the Data Processing and Scoring System 112 may retrieve the individual-level score that was previously with that UUID. Thus, all the individual-scores associated with the individual(s) in the request can be retrieved from the Database 114.

At step 4, the Data Processing and Scoring System 112 may send the individual-level scores back to the requesting issuers. In some embodiments, the existing channels and infrastructure may enable the Data Processing and Scoring System 112 to respond to issuer requests within 3 seconds (e.g., steps 2 through 4 may be performed within 3 seconds).

FIG. 3 is a chart of certain transaction attributes used in calculating individual-level scores. These are transaction attributes associated with transactional data that may be exclusive to the financial entity associated with a data processing and scoring system (e.g., the Data Processing and Scoring System 122). Some of these transaction attributes may be converted into single variables or combined into cross-variables for the calculation of the individual-level score.

In some embodiments, transaction attribute 302 is the number of months since the individual's first transaction. If the number of months is greater than 12, then the value of this is '12'. This can be turned into a single variable.

In some embodiments, transaction attribute 304 is a dummy variable associated with the individual's bank relations (e.g., if application bank is the primary transaction bank). If the application issuer is the main one in terms of transaction count over the last 12 months, then the value of this is '1', otherwise it is '0'. This can be turned into a single variable.

In some embodiments, transaction attribute 306 represents the transactions involving activation in top risk MCCs (e.g., pawn shops, betting, security brokers). In some embodiments, transaction attribute 308 is the average ticket size for transactions associated with the individual. Transaction attributes 306 and 308 can be combined into a cross variable 320.

In some embodiments, transaction attribute 310 represents share of medical transactions. In some embodiments, transaction attribute 312 represents share of construction transactions. Transaction attributes 310 and 312 can be combined into a cross variable 322.

In some embodiments, transaction attribute 314 represents the upscale consistency of transactions. In some embodiments, transaction attribute 316 represents insufficient funds decline rate. Transaction attributes 314 and 316 can be combined into a cross variable 324.

FIG. 4 illustrates an example formula for calculating individual-level scores.

In some embodiments, the example formula 400 for calculating individual-level scores and the probability of default for an individual involves a sigmoid function of [Intercept+(ATS>0)*beta_1+(ATS>300)*beta_2+ (ATS>400)*beta_3+(ATS>600)*beta_4+(months_ with_Visa>0)*gamma_1+(months_with_Visa>6)* gamma_2+(upscale>0)*delta_1+(upscale>1)*delta_2+(upscale>2)*delta_3+(upscale>3)*delta_4+(upscale>4)* delta_5+(upscale>5)*delta_6+relationship*epsilon+ (share>0)*zeta_1+(share>1)*zeta_2].

In the preceding formula, the value of the intercept and the coefficients (e.g., beta_1, beta_2, beta_3, beta_4, gamma_1, gamma_2, delta_1, delta_2, delta_3, delta_4, delta_5, delta_6, epsilon, zeta_1, and zeta_2) may be obtained by training the model (e.g., via a piecewise linear regression) using training data containing known probabilities of default.

The variables (ATS>0), (ATS>300), (ATS>400), and (ATS>600) may be dummy variables corresponding to a cross-variable (e.g., cross-variable 320) based on the average ticket size for an individual's transactions (e.g., transaction attribute 308) and activation in top risk MCCs (e.g., transaction attribute 306). For instance, the individual's average ticket size and activation in top risk MCCs can be combined in a certain manner to obtain a value for the cross-variable, which would fall into one of the bins (e.g., (ATS>0), (ATS>300), (ATS>400), and (ATS>600)). The value of the dummy variable corresponding to that bin would be set to '1', while the others would be set to '0'. As an example, if based on the individual's average ticket size and activation in top risk MCCs, the resulting cross-variable value is 500, then (ATS>400) will be '1' while (ATS>0), (ATS>300), and (ATS>600) may each be '0'.

The variables (months_with_Visa>0) and (months_ with_Visa>6) may be dummy variables associated with the number of months the individual has an account associated with the financial entity (e.g., transaction attribute 302) associated with the data processing and scoring system (e.g., the Data Processing and Scoring System 122). In this case, the financial entity is Visa. The number of months may fall into one of the bins (e.g., (months_with_Visa>0) and (months_with_Visa>6)). The value of the dummy variable corresponding to that bin would be set to '1', while the other would be set to '0'. Thus, if the individual had an account with Visa less than 6 months, then (months_with_Visa>0) will be '1' and (months_with_Visa>6) will be '0'. Otherwise, (months_with_Visa>0) will be '0' and (months_ with_Visa>6) will be '1'.

The variables (upscale>0), (upscale>1), (upscale>2), (upscale>3), (upscale>4), and (upscale>5) may be various dummy variables for the cross-variable (e.g., cross-variable 324) that is associated with the number of months with at least one transaction with a merchant classified as 'upscale' (specific MCCs) (e.g., transaction attribute 314) and the average number of insufficient funds declines per active month (e.g., transaction attribute 316). For instance, a purchase at a high-end jewelry store could be considered upscale. This upscale consistency in terms of number of months can be combined in a certain manner (not discussed) with the insufficient funds decline rate associated with the individual's transactions to determine a value for the cross-variable, which would fall into one of the bins (e.g., (upscale>0), (upscale>1), (upscale>2), (upscale>3), (upscale>4), and (upscale>5)). The value of the dummy variable corresponding to that bin would be set to '1', while the others would be set to '0'.

The variable 'relationship' may be a dummy variable associated with the bank relations (e.g., transaction attribute 304). If the application issuer is considered the main bank in terms of transaction count during the last 12 months, then this variable would be set to '1'. Otherwise it would be set to '0'.

The variables (share>0) and (share>1) may be various dummy variables for the cross-variable (e.g., cross variable 322) associated with both share of medical (e.g., transaction attribute 310) and share of construction (e.g., transaction attribute 312). For instance, the share of medical transactions can be combined in a certain manner with the share of construction transactions to obtain a value for the cross-variable, which would fall into one of the bins (e.g., (share>0) and (share>1)). The value of the dummy variable corresponding to that bin would be set to '1', while the other would be set to '0'.

FIG. 5 illustrates example transaction attribute values for individuals that are used in the individual-level score calculation. These are the same transaction attributes shown in FIG. 3.

In particular, these values may correspond to two individuals (e.g., example 1 and example 2). For instance, for transaction attribute 302, it can be seen that the first individual has made transactions for 13 months while the second individual has made transactions for 3 months. For transaction attribute 304, the application issuer is the main bank for individual 1 in terms of transaction count over the last 12 months, but this is not the case for individual 2. For transaction attribute 306, individual 1 did not make any transactions in pawn shops, betting, or security brokers over the last 12 months while individual 2 did. For transaction attribute 308, the average ticket size over the last 12 months for individual 1 is 700 P while the average ticket size over the last 12 months for individual 2 is 332 P. For transaction attribute 310, the share of medical transactional volume for individual 1 is 0.1, while for individual 2 it is 0.18. For transaction attribute 312, the share of construction transactional volume for individual 1 is 0.02, while for individual 2 it is 0.01. For transaction attribute 314, the number of months that individual 1 conducted at least one upscale transaction is 9, while with individual 2 it is 1. For transaction attribute 316, the average number of insufficient funds declines per month for individual 1 is 0, while for individual 2 it is 1.5.

FIG. 6 illustrates the corresponding single variable and cross-variable bins and values used in the individual-level score calculation for the transactional values shown in FIG. 5.

For instance, in FIG. 5, the transaction attribute 302 had values of 13 and 3, respectively, for individuals 1 and 2. The transaction attribute 302 corresponds to a single variable, which may correspond to the dummy variables (months_with_Visa>0) and (months_with_Visa>6) from the formula in FIG. 4 (e.g., the number of months the individual has an account associated with the financial entity associated with the data processing and scoring system). Thus, the chart in FIG. 6 shows that individual 1's transactional attribute 302 value of 13 would place the individual in the (months_with_Visa>6) bin, while individual 2's transactional attribute 302 value of 3 would place the individual in the (months_with_Visa>0) bin.

The transaction attribute 304 corresponds to a single variable associated with bank relations (e.g., if the application issuer is main in terms of transaction count over last 12 months), which may correspond to the dummy variable 'relationship' from the formula in FIG. 4. The chart in FIG. 5 shows that since individual 1 and individual 2 have transactional attribute 304 value of 'Main' and 'Not Main', respectively, the corresponding values for the dummy variable 'relationship' are '1' and '0' as seen in FIG. 6.

The transaction attributes 306 and 308 correspond to a cross-variable (e.g., cross-variable 320) associated with activation in top risk MCCs and average ticket size, which may correspond to the dummy variables (ATS>0), (ATS>300), (ATS>400), and (ATS>600) from the formula in FIG. 4. Although the formula for the cross-variable is not disclosed, FIG. 6 shows that the cross-variable value is 600 for individual 1 and 300 for individual 2.

The transaction attributes 310 and 312 correspond to a cross-variable (e.g., cross-variable 322) associated with share of medical volume and share of construction volume, which may correspond to the dummy variables (share>0) and (share>1) from the formula in FIG. 4. Although the formula for the cross-variable is not disclosed, FIG. 6 shows that the cross-variable value is 100 for both individual 1 and individual 2.

The transaction attributes 314 and 316 correspond to a cross-variable (e.g., cross-variable 324) associated with upscale consistency and insufficient funds decline rate, which may correspond to the dummy variables (upscale>0), (upscale>1), (upscale>2), (upscale>3), (upscale>4), and (upscale>5) from the formula in FIG. 4. Although the formula for the cross-variable is not disclosed, FIG. 6 shows that the cross-variable value is 6 for individual 1 and 1 for individual 2.

FIG. 7 illustrates example individual-level calculations based on the corresponding single variable and cross-variable bins shown in FIG. 6.

Assume that in FIG. 7, the "Coefficient" column provides the coefficients associated with each of the variables from the formula in FIG. 4. These coefficients are for demonstration purposes only, as the actual coefficients would be from modeling (e.g., via piecewise linear regression) based on training data of individuals containing knowledge of the target event (e.g., the actual default rates for those individuals).

The "Parameter" and "Value" columns correspond to the various variable/cross-variable bins from the formula in FIG. 4. For instance, the "upscale" parameter with "0" value corresponds to the (upscale>0) bin from the formula in FIG. 4. It can be seen that the associated coefficient is 1.23. Finally, a "1" in the column for E.g. #1 (individual 1) or E.g. #2 (individual 2) denotes which variables/cross-variables bins are associated with that individual's score calculation, based on the values for that individual's transaction attribute. Note that in this specific instance in FIG. 7, the 'relationship' parameter is inverted due to the '0' value, so the lack of a '1' in the column for individual 1 actually denotes that the application issuer is the main bank for individual 1. So in other words, for the formula shown in FIG. 4, individual 1 falls under the bins of (ATS>600), (months_with_Visa>6), (upscale>5), and (share>1), with relationship=1.

Thus, from the chart in FIG. 7 and the formula in FIG. 4, it can be determined that the calculation of the formula for individual 1 would be: −5.00+(1)*(0.23)+(1)*(0.18)+(1)*(0.43)+(1)*(0.33), which comes out to a linear score of −3.83. This corresponds to a probability of default of 0.02 and a default score of 776. Similarly, it can be determined that the calculation of the formula for individual 2 would be: −5.00+(1)*(0.66)+(1)*(0.48)+(1)*(0.98)+(1)*(0.21)+(1)(0.33), which comes out to a linear score of −2.34. This corresponds to a probability of default of 0.09 and a default score of 668.

Figure 8:
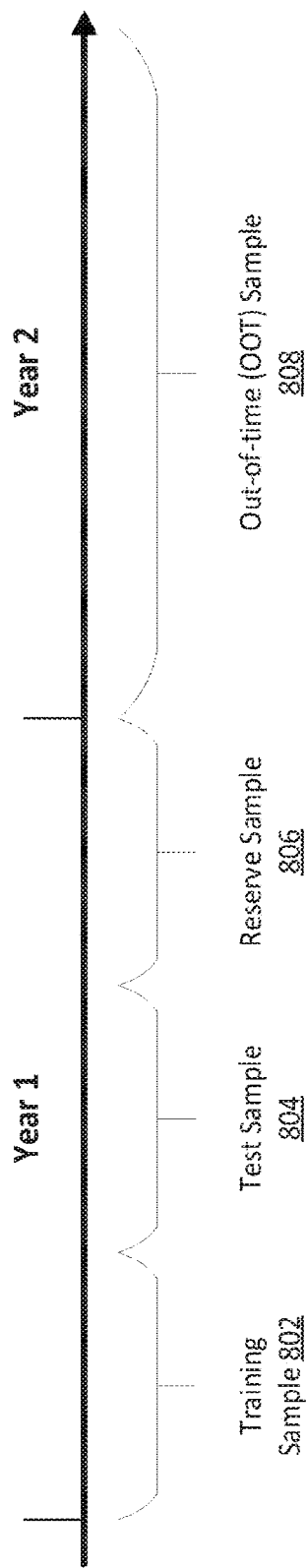
FIGS. 8-9 illustrate data sampling for the models used to calculate the individual-level scores, in accordance with certain embodiments.
Figure 9:
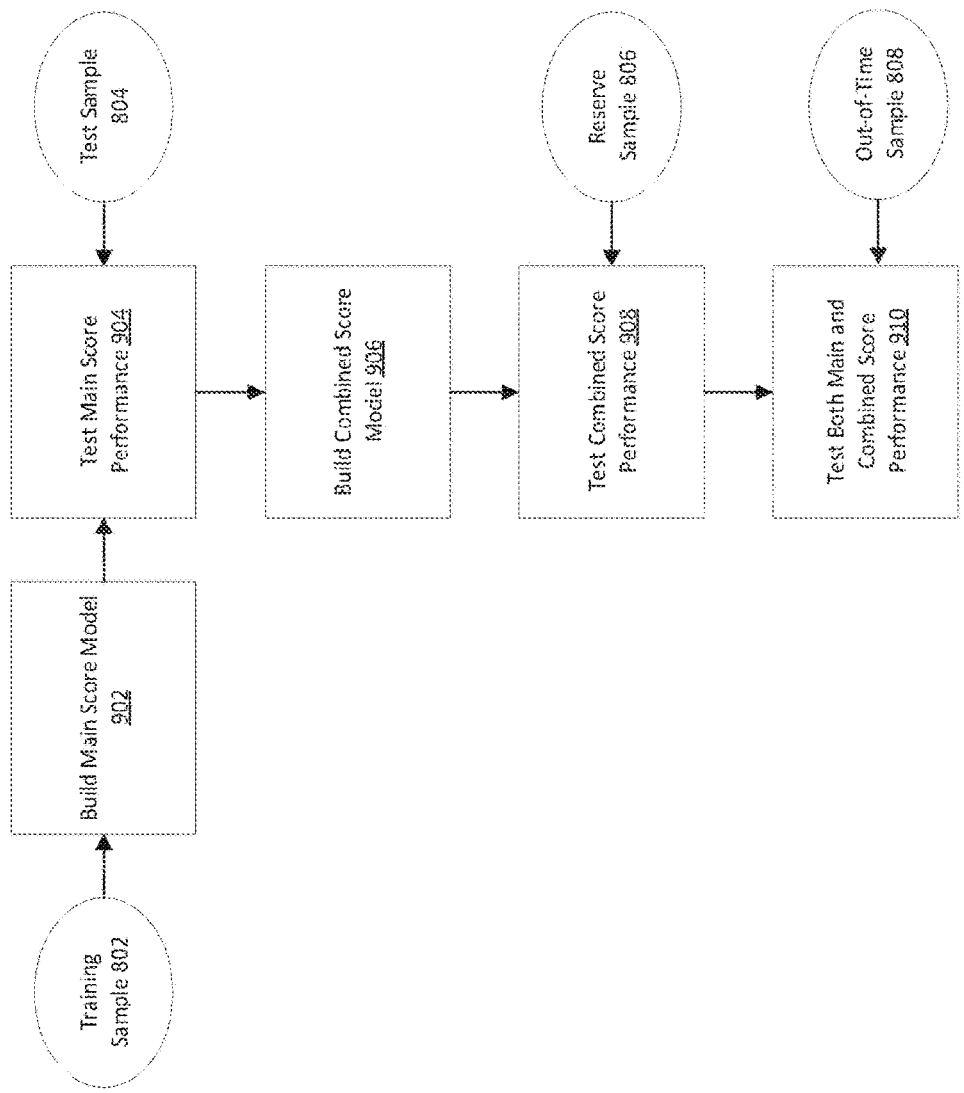

FIG. 8 illustrates data sampling for the models used to calculate the individual-level scores. In particular, the data can be taken from two consecutive years (e.g., year 1 and year 2). FIG. 9 illustrates how the sampled data is used to build the models for calculating the individual-level scores. FIGS. 8 and 9 are discussed in unison.

The training sample 802 can be randomly selected from a portion of year 1. At step 902, it can be seen that the training sample 802 can be used to build the main score model. The test sample 804 can also be randomly selected from another portion of year 1. At step 904, it can be seen that the test sample 804 can be used to test performance of the main score model. In some embodiments, at step 906, the main score model can be combined with another model (e.g., a combined scoring model), with the test sample used to build the combined scoring model.

The reserve sample 806 can be randomly selected from a portion of year 1. At step 908, it can be seen that the reserve sample 806 can be used to test performance of the combined scoring model. The out of time sample 808 can be taken from a portion of a completely different year (e.g., year 2). At step 910, it can be seen that the out of time sample 808 can be used to test the scoring performance of both the main score model and the combined scoring model.

Figure 10:
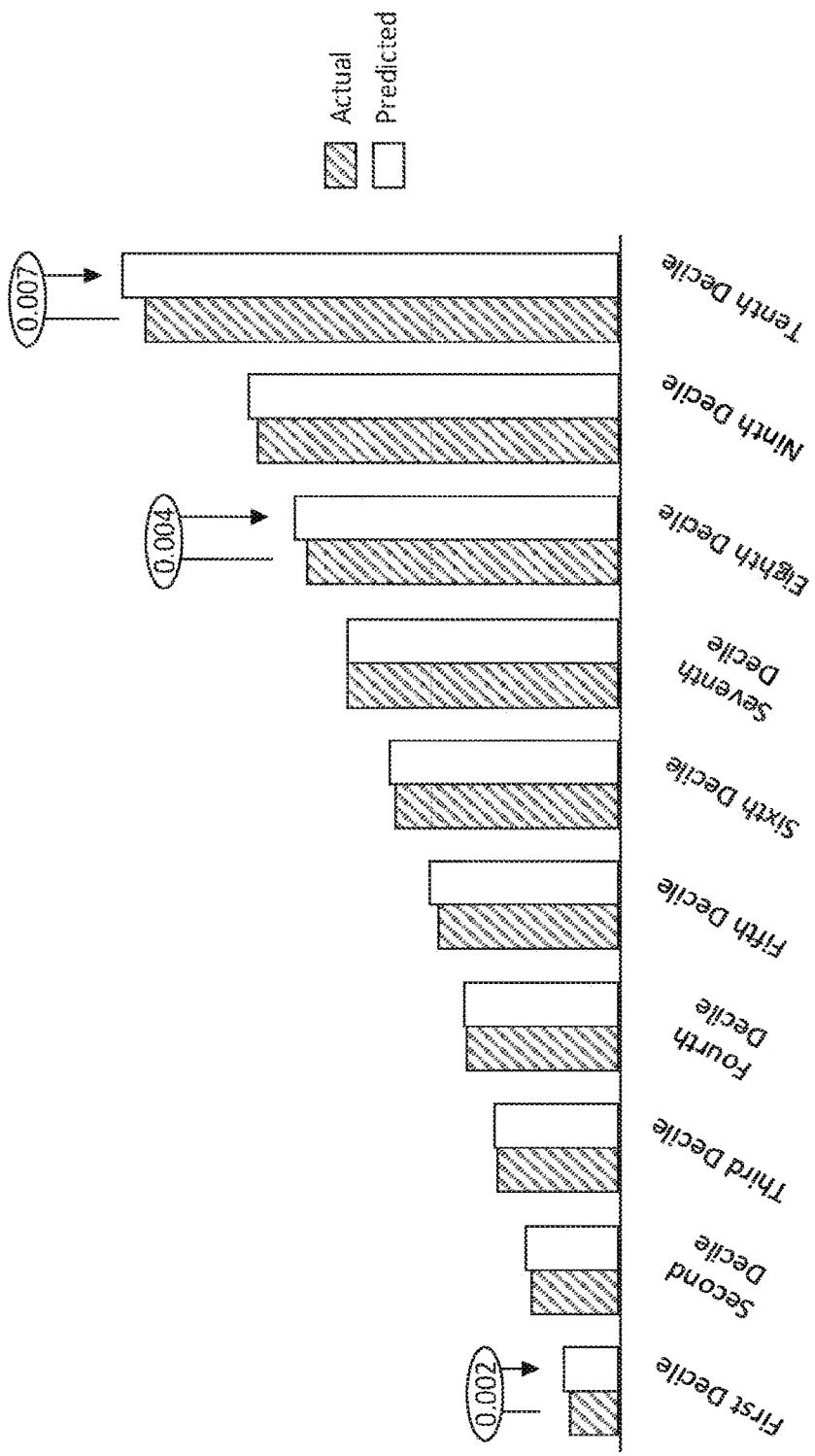
FIG. 10 is a graph comparing the predicted and actual default probabilities for individuals in a sample, in accordance with certain embodiments.

FIG. 10 is a graph comparing the predicted and actual default probabilities for individuals in a sample.

The individuals in a sample are broken into equal-sized deciles (e.g., ten buckets). In every group, the actual default rate and the predicted default rate (e.g., based on a model involving the transaction attributes associated with FIGS. 3 and 4) were compared. It can be seen that a model predicated on these specific transaction attributes (and variables/cross-variables) yields predicted default rates very close to actual default rates.

A computer system may be used to implement any or all of the entities or components described above. The subsystems of the computer system may be interconnected via a system bus. Additional subsystems such as a printer, keyboard, fixed disk (or other memory comprising computer readable media), monitor, which is coupled to display adapter, and others may be used. Peripherals and input/output (I/O) devices, which couple to an I/O controller (which can be a processor or other suitable controller), can be connected to the computer system by any number of means known in the art, such as a serial port. For example, a serial port or external interface can be used to connect the computer apparatus to a wide area network such as the Internet, a mouse input device, or a scanner. The interconnection via system bus allows the central processor to communicate with each subsystem and to control the execution of instructions from system memory or the fixed disk, as well as the exchange of information between subsystems. The system memory and/or the fixed disk may embody a computer readable medium. In some embodiments, the monitor may be a touch sensitive display screen.

A computer system can include a plurality of the same components or subsystems, e.g., connected together by an external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A method comprising:
   storing, by a first data processing system in communication with a plurality of issuers, data for each individual in a first set of individuals based on a unique user identifier (UUID) assigned to each individual in the first set of individuals, wherein the data comprises one or more hashed account data for each individual in the first set of individuals;
   transmitting, by the first data processing system to a second data processing system associated with a transaction processing system having access to transaction data, for each individual in the first set of individuals:
   the one or more hashed account data for the respective individual;
   the UUID for the respective individual; and
   target event data;
   training, by the second data processing system, a predictive model with a training sample of transaction data including a known metric for individuals in the training sample of transaction data;
testing, by the second data processing system, a testing sample of transaction data including a known metric for individuals in the testing sample of transaction data;
collecting, by the second data processing system, transaction data associated with each individual in the first set of individuals using at least the hashed account data and the UUID without using personal data associated with the first set of individuals, wherein at least a subset of the training sample of transaction data, the testing sample of transaction data and the transaction data associated with each individual is access restricted outside the second data processing system;
applying, by the second data processing system, the trained and tested predictive model to the transaction data associated with each individual in the first set of individuals in order to calculate an individual-level score associated with the respective individual, wherein the trained and tested predictive model is configured to determine a predicted metric for an individual based on a set of transactional attributes in the transaction data associated with the respective individual;
calculating, by the second data processing system, the individual-level score associated with the respective individual; and
transmitting, by the second data processing system, the individual-level score associated with the respective individual to an issuer via the first data processing system, wherein the individual-level score is indicative of a predicted default rate for an account to be issued by the issuer.

2. The method of claim 1, wherein the set of transactional attributes including two or more of:
a number of months since a first transaction performed by the respective individual;
a bank relation associated with the respective individual;
a top risk activation indication associated with the respective individual, wherein the top risk activation indication is based on any transactions with high-risk merchants performed over last twelve months by the respective individual;
an average ticket size for all transactions performed over the last twelve months by the respective individual;
a share of medical-related transactions out of all transactions performed over the last twelve months by the respective individual;
a share of construction-related transactions out of all transactions performed over the last twelve months by the respective individual;
a number of months with at least one upscale transaction performed by the respective individual; and
an average number of insufficient funds declines per active month experienced by the respective individual.

3. The method of claim 1, further comprising:
receiving, at the first data processing system, updated data associated with the first set of individuals; and
storing, by the first data processing system, the updated data for each individual in the first set of individuals based on the UUID for the respective individual.

4. The method of claim 3, further comprising:
transmitting, by the first data processing system to the second data processing system, the updated data for each individual in the first set of individuals.

5. The method of claim 4, wherein the updated data comprises past default events associated with the respective individual.

6. The method of claim 1, wherein the transaction data is associated with a primary account number.

7. The method of claim 1, wherein the target event data includes any past default events associated with the respective individual.

8. The method of claim 1, wherein the predictive model is a supervised machine learning model.

9. The method of claim 1, further comprising:
receiving, from the second data processing system, a plurality of scores corresponding one-to-one with the first set of individuals, storing the plurality of scores in a database;
receiving, from the issuer, a request for a score for an individual;
locating the score for the individual among the plurality of scores in the database; and
sending, to the issuer, the score for the individual.

10. The method of claim 9, further comprising:
receiving an updated plurality of scores corresponding one-to-one with the first set of individuals; and
updating the plurality of scores in the database based on the updated plurality of scores.

11. The method of claim 9, wherein the request for the score for the individual includes the unique user identifier (UUID) associated with the individual, and wherein the score for the individual is stored in the database based on the UUID associated with the individual.

12. The method of claim 9, wherein the receiving, locating, and sending steps are performed within a total of three seconds.

13. The method of claim 9, wherein the plurality of scores are factored into a combined scoring model to obtain a plurality of combined scores corresponding one-to-one with the first set of individuals.

14. A computer system comprising:
a first data processing system comprising a first processor and a first computer-readable memory containing program instructions that, when executed by the first processor, cause the first processor to:
store data for each individual in a first set of individuals based on a unique user identifier (UUID) assigned to each individual in the first set of individuals, wherein the data comprises one or more hashed account data for each individual in the first set of individuals;
transmit, to a second data processing system associated with a transaction processing system having access to transaction data, for each individual in the first set of individuals:
the one or more hashed account data for the respective individual;
the UUID for the respective individual; and
target event data; and
the second data processing system comprising a second processor and a second computer-readable memory containing program instructions that, when executed by the second processor, cause the second processor to:
train a predictive model with a training sample of transaction data including a known metric for individuals in the training sample of transaction data;
test a testing sample of transaction data including a known metric for individuals in the testing sample of transaction data;
collect transaction data associated with each individual in the first set of individuals using at least the hashed account data and the UUID without using personal data associated with the first set of individuals, wherein at least a subset of the training sample of transaction data, the testing sample of transaction data and the transaction data associated with each individual is access restricted outside the second data processing system;

apply the trained and tested predictive model to the transaction data associated with each individual in the first set of individuals in order to calculate an individual-level score associated with the respective individual, wherein the trained and tested predictive model is configured to determine a predicted metric for an individual based on a set of transactional attributes in the transaction data associated with the respective individual;

calculate the individual-level score associated with the respective individual; and transmitting, by the second data processing system, the individual-level score associated with the respective individual to an issuer via the first data processing system, wherein the individual-level score is indicative of a predicted default rate for an account to be issued by the issuer.

15. The computer system of claim 14, wherein the program instructions, when executed by the first processor, further cause the first processor to receive, at the first data processing system, updated data associated with the first set of individuals; and store the updated data for each individual in the first set of individuals based on the UUID for the respective individual.

16. The computer system of claim 15, wherein the updated data includes any past default events associated with the respective individual.

17. The computer system of claim 14, wherein the transaction data is associated with a primary account number.

18. The computer system of claim 14, wherein the target event data comprises past default events associated with the respective individual.

19. The computer system of claim 14, wherein the program instructions, when executed by the first processor, further cause the first processor to:

receive, the second data processing system, a plurality of scores corresponding one-to-one with the first set of individuals;

receive, from the issuer, a request for a score associated with an individual; and transmit, to the issuer, the score associated with the individual.

20. A method comprising:

receiving, by a data processing system associated with a transaction processing system having access to transaction data, for each individual in a first set of individuals:

one or more hashed account data for the respective individual;

a UUID for the respective individual; and a target event data;

training, by the data processing system, a predictive model with a training sample of transaction data including a known metric for individuals in the training sample of transaction data;

testing, by the data processing system, a testing sample of transaction data including a known metric for individuals in the testing sample of transaction data;

collecting, by the data processing system, transaction data associated with each individual in the first set of individuals using at least the hashed account data and the UUID without using personal data associated with the first set of individuals, wherein at least a subset of the training sample of transaction data, the testing sample of transaction data and the transaction data associated with each individual is access restricted outside the data processing system;

applying, by the data processing system, the trained and tested predictive model to the transaction data associated with each individual in the first set of individuals in order to calculate an individual-level score associated with the respective individual, wherein the trained and tested predictive model is configured to determine a predicted metric for an individual based on a set of transactional attributes in the transaction data associated with the respective individual; and calculating, by the data processing system, the individual-level score associated with the respective individual; and transmitting, by the data processing system, the individual-level score associated with the respective individual to an issuer, wherein the individual-level score is indicative of a predicted default rate for an account to be issued by the issuer.

* * * * *